US00PP34428P2

(12) United States Plant Patent
Lee

(10) Patent No.: US PP34,428 P2
(45) Date of Patent: Jul. 19, 2022

(54) ***IMPATIENS* PLANT NAMED 'IMGZ0022'**

(50) Latin Name: ***Impatiens* interspecific**
Varietal Denomination: 'IMGZ0022'

(71) Applicant: SYNGENTA CROP PROTECTION AG, Basel (CH)

(72) Inventor: Jaemin Lee, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/300,517

(22) Filed: Jul. 26, 2021

(51) Int. Cl.
*A01H 5/02* (2018.01)
*A01H 6/16* (2018.01)

(52) U.S. Cl.
USPC ..... Plt./318.2

(58) Field of Classification Search
USPC ..... Plt./318.2
CPC ... A01H 5/02; A01H 5/00; A01H 6/16; A01H 6/165; A01H 6/56
See application file for complete search history.

(56) References Cited

PUBLICATIONS

Upov Pluto Plant Variety Database Sep. 23, 2021, retrieved on Sep. 28, 2021, retrieved from the Internet at https://www.upov.int/pluto/en/index.jsp, one page. (Year: 2021).*

* cited by examiner

*Primary Examiner* — June Hwu
(74) *Attorney, Agent, or Firm* — Dale Skalla

(57) ABSTRACT

A new *Impatiens* plant named 'IMGZ0022' particularly distinguished by the white flower on short peduncles on a medium sized well branched plant with deep dark green foliage.

1 Drawing Sheet

Latin name of the genus and species of the plant claimed: *Impatiens* interspecific.

Varietal denomination: 'IMGZ0022'.

BACKGROUND OF THE NEW PLANT

The present invention comprises a new *Impatiens*, botanically known as *Impatiens* interspecific, and hereinafter referred to by the variety name 'IMGZ0022'.

'IMGZ0022' is a product of a planned breeding program. The new cultivar has large, flat, white flowers. The foliage is deep dark green with light green veins on the upper and lower side of the leaf. The plant is medium sized and well branched.

'IMGZ0022' originated from a hybridization made in March 2017 in a controlled breeding environment in San Jose Pinula, Guatemala.

The female parent is designated as 'W5516-2' with white flower color. The male parent is designated as 'W5590-5' and is large sized and has white flower pattern.

The resultant seed was sown in November 2017 in a greenhouse in Gilroy, Calif. USA and 'IMGZ0022' was selected there as one flowering plant within the progeny of the stated cross in spring 2017.

The first act of asexual reproduction of 'IMGZ0022' was accomplished when vegetative cuttings were propagated from the initial selection in February 2018 in a controlled environment in Gilroy, USA.

BRIEF SUMMARY OF INVENTION

Horticultural examination of plants grown from cuttings of the plant initiated in April 2018 in Gilroy, Calif. USA, has demonstrated that the combination of characteristics as herein disclosed for 'IMGZ0022' are firmly fixed and are retained through successive generations of asexual reproduction.

'IMGZ0022' has been observed under different environmental conditions. The phenotype may vary significantly with variations in environment such as temperature and light intensity.

A Plant Breeder's Right for this cultivar was applied for in Canada on Aug. 4, 2021, No. 21-10688. 'IMGZ0022' has not been made publicly available prior to the effective filing date of this application, notwithstanding any disclosure that may have been made less than one year prior to the effective filing date of this application by the inventor or another who obtained 'IMGZ0022' directly from the inventor.

The following traits have been repeatedly observed and are determined to be basic characteristics of the new variety. The combination of these characteristics distinguishes this *Impatiens* as a new and distinct variety.

BRIEF DESCRIPTION OF THE PHOTOGRAPHS

The accompanying photographic drawings show typical flower and foliage characteristics of 'IMGZ0022' with colors being as true as possible with an illustration of this type.

Figure 1:
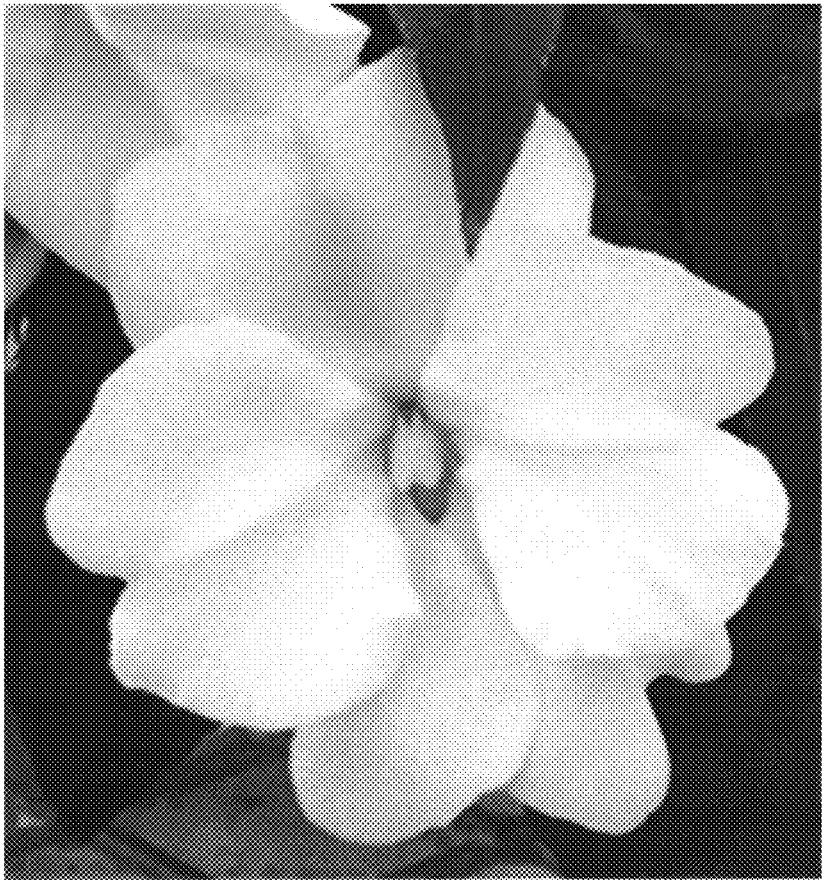
Figure 2:
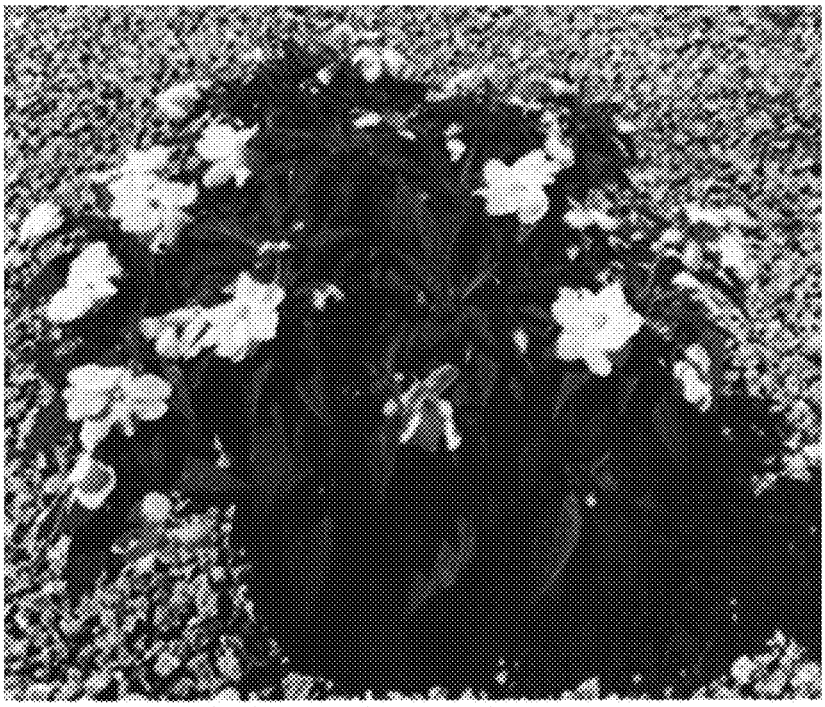

The photographic drawings show in FIG. 1 a close-up of the flowers and in FIG. 2 a flowering plant of the new variety growing in 14 cm pot.

DETAILED BOTANICAL DESCRIPTION

The aforementioned photographs were taken in March 2021 from plants grown in a greenhouse trial in Gilroy, Calif. USA. These plants were growing in 10 cm pots and were approximately 16 weeks of age.

The plant descriptions and measurements were taken in May 2021, on 16 week old plants growing in a greenhouse in Gilroy, Calif. USA. Cuttings were stuck in week 2 for rooting, planted into 10 cm pots in week 6, and were grown, without pinching, on benches in a greenhouse, initially at a day temperature of 18° C. and night temperature of 16° C. However, day temperatures often raised above 20° C.

TABLE 1

DIFFERENCES BETWEEN THE NEW VARIETY 'IMGZ0022' AND SIMILAR PATENTED VARIETIES

| | 'IMGZ0022' | 'NG143' ('Sonic White') | 'NG091' ('Sonic Deep Red') |
|---|---|---|---|
| Flower color: | White | White | Deep red |
| Flower pattern: | Solid white color | Solid white color | Solid white color |
| Habit/vigor: | Medium | Medium | Vigor |
| Branching: | Better | Less | Less |

Plant:

*Form, growth and habit.*—Medium sized, well-mounded, well branched.

*Plant height.*—17.0 cm (without pot), 27 cm (with pot).

*Plant height (inflorescence included).*—17.0-18.0 cm (without pot).

*Plant width.*—39.0 cm

Roots:

*Number of days to initiate roots.*—5-6 days at about 22 degrees C.

*Number of days to produce a rooted cutting.*—14-16 days at 22 degrees C.

*Type.*—Fibrous, free branching

*Color.*—RHS 159A

Foliage:

*Arrangement.*—Simple leaves, mainly in whorls.

*Young leaf, color upper surface.*—RHS 137A.

*Young leaf, color lower surface.*—Closest RHS 146A.

*Mature leaf, color upper surface.*—RHS 139A.

*Mature leaf, color lower surface.*—Closest to RHS 146A.

*Upper leaf surface presence of any markings and anthocyanim coloration.*—Very weak.

*Length.*—Up to 8.8 cm.

*Width.*—Up to 3 cm.

*Shape.*—Lanceolate.

*Base shape.*—Rounded.

*Apex shape.*—Acuminate.

*Margin.*—Serrulate, with short bristles.

*Texture.*—Slightly waxy and glossy on the upper surface, glabrous on both surfaces.

*Color of veins, upper surface.*—RHS 138A.

*Color of veins, lower surface.*—RHS 145A.

*Petiole color, upper side.*—RHS 138B.

*Petiole color, lower side.*—RHS 138C.

*Length.*—Up to 2.5 cm.

*Diameter.*—0.3 cm.

*Texture.*—Glabrous.

Stem:

*Color of stem.*—RHS 137C.

*Length of stem.*—About 15 cm.

*Diameter.*—1.3 cm.

*Length of internodes.*—Approximately 2 to 4 cm.

*Texture.*—Smooth, glabrous.

*Number of branches.*—6 main branches plus 9 side branches per main branch.

*Color of peduncle.*—RHS 144A.

*Length of peduncle.*—4.8-5.2 cm.

*Peduncle diameter.*—0.3 cm.

*Texture.*—Glabrous.

Inflorescence:

*Blooming habit.*—Continuous flowering from late spring through fall.

*Type of inflorescence.*—Solitary flowers emerge from the upper leaf nodes of the stem.

*Number of flowers per node.*—2-4 open flowers and additional buds in various stages of development.

*Quantity of flowers per plant.*—16 open flowers plus 20 (big and small) buds (10 cm pot plant in October).

*Average number of petals per flower.*—5 petals.

*Average size of the upper petal, lateral petal and lower petal.*—Upper petal=3.0 cm, lateral petal=2.4 cm, and lower petal=2.5 cm.

*Lastingness of individual blooms on the plant.*—About 8-10 days.

*Fragrance.*—None.

Bud (just before opening):

*Color.*—RHS 157C WITH RHS 142B.

*Length.*—Up to 1.8 cm.

*Width.*—Up to 1.4 cm.

*Shape.*—Ovate.

Immature flowers:

*Color of petals, upper surface.*—RHS 155C.

*Color of petals, lower surface.*—RHS 157D.

Mature flowers:

*Flower, vertical length.*—7.5 cm.

*Flower, horizontal width.*—7.0 cm.

*Flower depth.*—0.8-1.0 cm.

*Color of petals, upper surface.*—RHS 157D.

*Color of petals, lower surface.*—RHS 155C.

*Depth of incision of lower petal.*—Deep.

*Petal shape.*—Heart shaped.

*Petal apex shape.*—Broadly obcordate.

*Petal margin.*—Entire.

*Petal texture, upper surface.*—Papillose.

*Petal texture, lower surface.*—Papillose.

Calyx:

*Arrangement.*—One large sepal bearing the spur, 2 small, lateral sepals, and 1 fused keel.

*Large sepal(s).*—

*Color, visible surface.*—RHS 157C.

*Length.*—1.6 cm.

*Width.*—1.2 cm.

*Shape.*—Ovate.

*Apex shape.*—Aristate.

*Base.*—Fused with the spur.

*Margins.*—Entire.

*Texture, upper surface.*—Papillose.

*Texture, lower surface*.—Papillose.
*Lateral sepals*.—
*Color of surface*.—RHS 145C.
*Length*.—1.2 cm.
*Width*.—0.6-0.7 cm.
*Shape*.—Ovate.
*Apex shape*.—Acuminate.
*Base*.—Fused.
*Margins*.—Entire.
*Texture, upper surface*.—Glabrous.
*Texture, lower surface*.—Glabrous.
*Keel color*.—From RHS 46A to more brownish tones, closest to RHS 185A.

Spur:
*Color*.—RHS 145C.
*Length*.—6.1-6.3 cm.
*Diameter*.—0.3 cm at the base, 0.1 cm at tip.
*Curvature of the spur*.—Medium.

Reproductive organs:

Androecium: 5 stamen, fused with the anthers hooded.
*Diameter of androecium*.—0.7 cm.
*Surface color*.—RHS 157B, fading towards margin.
*Pollen amount*.—Moderate.
*Color of pollen*.—RHS 8D.

Gynoecium:
*Pistil*.—One, elongate.
*Pistil length*.—0.6 cm.
*Stigma color*.—RHS 145A.
*Ovary color*.—RHS 141B.
*Fertility/seed set*.—Has not been observed on this hybrid.
*Disease/pest resistance*.—Has not been observed on this hybrid. However, it is known for *Impatiens* New Guinea that it is downy mildew resistant.

What is claimed is:

1. A new and distinct variety of *Impatiens* plant named 'IMGZ0022' substantially as illustrated and described herein.

* * * * *